United States Patent [19]

Beatty

[11] Patent Number: 5,335,449
[45] Date of Patent: Aug. 9, 1994

[54] DELIVERY SYSTEM FOR AN AGRICULTURALLY ACTIVE CHEMICAL

[75] Inventor: Charles L. Beatty, Gainesville, Fla.

[73] Assignee: Net/Tech International, Inc., Baldwin, N.Y.

[21] Appl. No.: 745,635

[22] Filed: Aug. 15, 1991

[51] Int. Cl.$^5$ ............................................ A01G 29/00
[52] U.S. Cl. ........................................ 47/48.5; 47/66
[58] Field of Search ............................... 47/48.5, 66

[56] References Cited

U.S. PATENT DOCUMENTS

| | | |
|---|---|---|
| 2,222,815 | 11/1940 | Johnson .............................. 47/66 |
| 3,771,377 | 11/1956 | Greminger et al. . |
| 2,858,647 | 11/1958 | Cotton . |
| 2,965,508 | 12/1960 | Windover et al. . |
| 4,031,179 | 6/1977 | Tatzel et al. . |
| 4,508,595 | 4/1985 | Gasland . |
| 4,698,264 | 10/1987 | Steinke . |
| 4,744,976 | 5/1988 | Snipes et al. . |
| 4,765,982 | 8/1988 | Ronning et al. . |
| 4,780,317 | 10/1988 | Sekikawa et al. . |
| 4,806,337 | 2/1989 | Snipes et al. . |
| 4,851,227 | 7/1989 | Markus et al. . |
| 4,888,145 | 12/1989 | Allner et al. . |
| 4,889,719 | 12/1989 | Ohtsubo et al. . |
| 4,891,223 | 1/1990 | Ambegaonkar et al. . |
| 5,039,524 | 8/1991 | Oishi et al. . |

FOREIGN PATENT DOCUMENTS

| | | |
|---|---|---|
| 1103389 | 2/1968 | United Kingdom . |
| 1269622 | 4/1972 | United Kingdom . |
| 1371096 | 10/1974 | United Kingdom . |
| 1371179 | 10/1974 | United Kingdom . |
| 2027346 | 2/1980 | United Kingdom . |
| 2052544 | 3/1983 | United Kingdom . |

Primary Examiner—Thuy M. Bui
Assistant Examiner—Joanne C. Downs
Attorney, Agent, or Firm—R. Neil Sudol; Henry D. Coleman

[57] ABSTRACT

A delivery system for an agriculturally active chemical comprises a body or carrier portion including a first water dispersible agriculturally inert and essentially nontoxic composition containing a predetermined aliquot of the agriculturally active chemical. The body or carrier portion has a predetermined size and a predetermined shape. The delivery system also comprises a protective coating, about the body portion, of a second water dispersible agriculturally inert and essentially nontoxic composition. The aliquot of the agriculturally active chemical is an amount of the agriculturally active chemical effective to terminate functioning of a target agricultural pest upon application of the agriculturally active chemical to soil or water via the delivery system. The agriculturally active chemical can take the form of a biocide such as an insecticide, fungicide or nemacide. More particularly, the agriculturally active chemical is a compound taken from the group consisting of dimethoate, vydate, vendex, metasystox-R, fluvalinate and kethane, invermectin, propoxur, chlorpyrifos, diazinon, malathion, carbaryl, fenvalerate, methomyl, acephate, permethrins, and diflubenzuron.

22 Claims, 2 Drawing Sheets

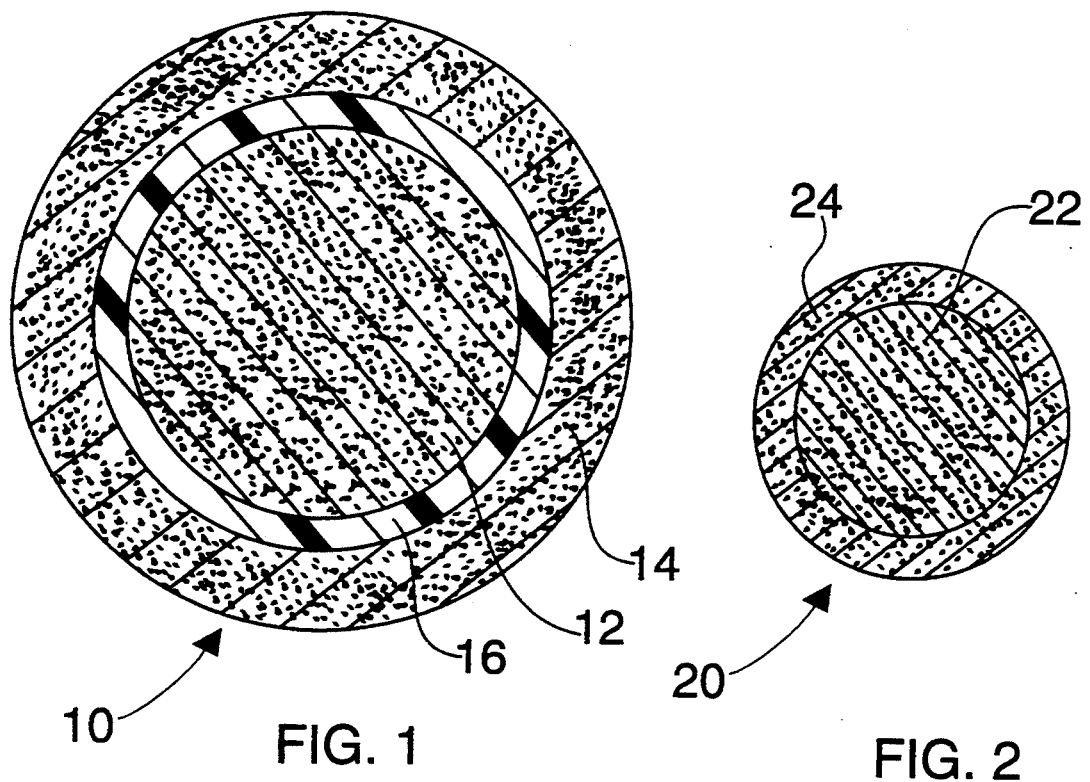
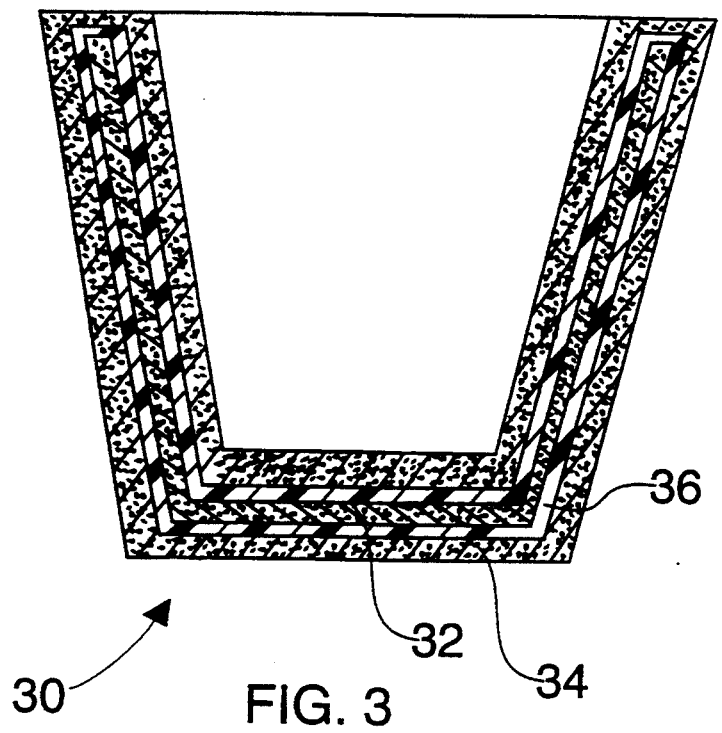

DELIVERY SYSTEM FOR AN AGRICULTURALLY ACTIVE CHEMICAL

BACKGROUND OF THE INVENTION

This invention relates to a delivery system for a biocide such as an insecticide, fungicide, nemacide, herbicide or other pesticide. This invention also relates to a method of making such a delivery system.

The dangers of using biocides such as insecticides, fungicides, nemacides or other pesticides are largely known. Generally, such substances pose significant, if not substantial, threat to human beings who come into contact with the chemicals during manufacturing or application of the chemical to a target to be treated, for example, agricultural crops. Great care must be taken in tapping the transport drums and in mixing the chemicals with water prior to a spraying or other distribution operation. Protecting workers from the dangers of the chemicals gives rise to delays and concomitantly increased expense of agricultural production.

Although on a reduced scale, similar dangers exist in the home-use market. Chemicals for the home market are also shipped in liquid form, in smaller containers. The chemicals must be mixed with water and otherwise handled, which increases the risk of harm to the user and even to innocents such as children.

OBJECTS OF THE INVENTION

An object of the present invention is to provide an essentially non-toxic delivery system for an agriculturally active chemical, especially a biocide.

A more particular object of the present invention is to provide such a delivery system wherein human contact with the biocide is reduced, if not eliminated.

Another particular object of the present invention is to provide such a delivery system which is utilizable in home use applications, as well as in large-scale agricultural applications.

An additional object of the present invention is to provide a delivery system for a delayed release of an biocide.

A further particular object of the present invention is to provide a delivery system which is essentially agriculturally inert, except for the agriculturally active chemical to be delivered or applied.

Yet another object of the present invention is to provide a method for making a delivery system for an agriculturally active chemical.

A more specific object of the present invention is to provide such a method wherein the delivery system can be made in different shapes.

SUMMARY OF THE INVENTION

A delivery system for an agriculturally active chemical, particularly a biocide such as an insecticide, a nemacide, a herbicide or other pesticide, comprises, in accordance with the present invention, a body portion including a first water dispersible agriculturally inert and essentially nontoxic composition containing a predetermined aliquot of the agriculturally active chemical. The body portion has a predetermined size and a predetermined shape. The delivery system also comprises a protective coating, about the body portion, of a second water dispersible agriculturally inert and essentially nontoxic composition. The aliquot of the agriculturally active chemical is an amount of the agriculturally active chemical effective to substantially terminate the biological functioning of a significant number of target agricultural pests upon application of the biocide to soil via the delivery system.

The body portion preferably takes the shape of a pellet for certain home use and large-scale agricultural applications. Because the pellets are provided with a protective coating of a nontoxic composition, no special or extraordinary precautions need be taken for the transport and handling of the pellets. Shipping containers may be recycled or disposed of in any ecologically suitable manner. The pellets themselves may be handled by hand without danger of contamination by the agriculturally active chemical.

A number of pellets is selected by the user in accordance with the size of the application. For example, doubling the area to be protected generally requires double the number of pellets. The selected pellets are simply placed into a container of water and allowed to disperse. Upon dispersion of the pellets, the agriculturally active chemical becomes dissolved in the water. The residue from the agriculturally inert and essentially nontoxic compositions is partially dissolved, partially suspended in solution and may precipitate out to a minor extent. The residue, however, is essentially completely dispersible in water and does not clog spraying or other application equipment.

The term "agricultrually active chemical" is used throughout this specification to describe a biologically active chemical which has use in agriculture. Such compounds may include biocides, but may also include chemicals which promote or modify the growth of plants. These compounds may be natural or synthetic chemicals and may include biochemicals such as genetically engineered products.

In some applications, the body portion of the delivery system takes the form of a container, for example, a pot or other cup-shaped receptacle, in which a seedling may be placed. The receptacle with its contents is then placed in the soil and eventually disperses with rain and watering, so that the agriculturally active chemical is gradually applied in the soil about the seedling.

The agriculturally active chemical is preferably a biocide such as an insecticide, fungicide, nemacide or herbicide. More particularly, the agriculturally active chemical is a compound taken from the group consisting of dimethoate, vydate, vendex, metasystox-R, fluvalinate and kethane, invermectin, propoxur, chlorpyrifos, diazinon, malathion, carbaryl, fenvalerate, methomyl, acephate, permethrins, and diflubenzuron.

Dimethoate (CYGON), vydate, vendex, metasystox-R, fluvalinate (MAVRIK) and kethane are particularly suitable for placement into the soil in a shipment container. If the soil is kept moist for shipping, the pesticide would be released slowly and continuously from the water-dispersible material during shipment and the plants in the containers would be insect free upon arrival at their destinations.

Invermectin is suitable for use as a nemacide. The water dispersible substrate carries the nemacide by discing into soil near the roots of a plant. Watering will then allow direct interaction with nemas.

Propoxur (BAYGON), chlorpyrifos (DURSBAN), diazinon, malathion, carbaryl (SEVIN) are considered suitable for home-use applications. For both indoor and outdoor spraying, a predetermined number of pellets is dissolved in water and eliminates many hazards and inconveniences associated with home spraying.

Chlorpyrifos (LORSBAN), fenvalerate (PYDRIN), methomyl (LANNATE, NUDRIN), acephate (ORTHENE), permethrins (AMBUSH, POUNCE), and diflubenzuron (DIMILIN) are useful in pre-packaged biologically degradable carriers as described herein, particularly for small farmers to conform to many new regulations on pesticides.

Pursuant to a particular embodiment of the present invention, the agriculturally active chemical is interspersed throughout the first water dispersible agriculturally inert and essentially nontoxic composition. This embodiment is especially advantageous for applications calling for a gradual release of the biocide over a period of time. After the protective coating is dispersed, the body portion of the delivery system gradually disperses and releases the agriculturally active chemical.

Pursuant to an alternative embodiment of the present invention, the body portion is hollow and defines a chamber, the agriculturally active chemical being disposed at least partially within the chamber.

Pursuant to another feature of the present invention, at least one of the water dispersible agriculturally inert and essentially nontoxic compositions includes cellulose ether, stearic acid or one of its related salt compositions, and cellulose fiber. The term "cellulose ether" is used herein to designate hydroxymethyl cellulose, hydroxyethyl cellulose, hydroxypropyl cellulose, or any mixture thereof. The related stearic salt compositions include potassium stearate, sodium stearate and zinc stearate.

The cellulose fiber preferably comprises between approximately 20% and 75% by weight of the respective first water dispersible agriculturally inert and essentially nontoxic composition. The cellulose ether preferably comprises between approximately 10% and 65% by weight of that water dispersible agriculturally inert and essentially nontoxic composition. In addition, the stearic acid or stearate preferably comprises between approximately 4% and 25% by weight of the water dispersible agriculturally inert and essentially nontoxic composition.

The cellulose fiber may take the form of shredded tissue paper or unbleached cellulose fiber. Additional components such as diluents, dispersants, surfactants and other additives may be included within the nontoxic compositions for use in the present invention.

For example, pursuant to another feature of the present invention, either or both of the water dispersible agriculturally inert and essentially nontoxic compositions further include calcium carbonate and/or polyvinylalcohol. The calcium carbonate preferably comprises between approximately 5% and 10% of the respective water dispersible agriculturally inert and essentially nontoxic composition. The polyvinylalcohol preferably comprises between approximately 5% and 15% of the respective water dispersible agriculturally inert and essentially nontoxic composition.

Pursuant to another feature of the present invention, the first water dispersible agriculturally inert and essentially nontoxic composition may further include a surfactant.

According to another embodiment of the present invention, a layer of a water soluble polymer is disposed between the body portion and the coating. The polymer interlayer functions to prevent or inhibit diffusion of the agriculturally active chemical from the inner body portion of the delivery system into the protective coating. The polymer interlayer preferably comprises one or more of the following: acrylics, polyvinylidene chloride, ionomer, polyvinylalcohol, and polyethylhydroxycellulose.

A method for making a delivery system for an agriculturally active chemical comprising, in accordance with the present invention, the step of forming a body portion including a first water dispersible agriculturally inert and essentially nontoxic composition which contains a predetermined aliquot of the agriculturally active chemical. The body portion has a predetermined size and a predetermined shape. In another step, a protective coating of a second water dispersible agriculturally inert and essentially nontoxic composition is placed about the body portion. The aliquot of the agriculturally active chemical is an amount effective to substantially terminate the functioning of a significant number of target agricultural pests upon application of the agriculturally active chemical to the area to be treated (e.g., soil, crops, a body of water) via the delivery system.

In accordance with another feature of the present invention, the step of forming the body portion includes the steps of (a) providing a first dough including water, the first water dispersible agriculturally inert and essentially nontoxic composition and a predetermined amount of the agriculturally active chemical, (b) forming the dough into the body portion, and (c) drying the body portion while the dough is maintained in the predetermined shape. Pursuant to this manner of forming the body portion of the delivery system, the agriculturally active chemical is combined with the ingredients of the first dough prior to the shaping and drying of the dough. The dough may be molded, sculpted, extruded, pressed or otherwise shaped to form any of a variety of different shapes. A pellet and a pot or cup shape are two preferred forms for the delivery system.

In accordance with another feature of the present invention, the step of placing the protective coating about the chemical-bearing body portion comprises the steps of (i) providing a second dough including water and the second water dispersible agriculturally inert and essentially nontoxic composition, (ii) applying the second dough in a layer about the dried body portion, and (iii) drying the layer of the second dough about the body portion.

The application of the second dough to the dried core or chemical-bearing body portion may be implemented by any suitable technique. For example, the dried body portion may be dipped into a vat of the second dough and then removed from the vat with a layer of the second dough. The second dough may also be molded or pressed about the dried shapes of the body portions.

In accordance with an alternative feature of the present invention, the step of forming the body portion includes the steps of (a) providing a first dough including water and the first water dispersible agriculturally inert and essentially nontoxic composition, (b) shaping the first dough into a container preform, (c) drying the preform, (d) providing the aliquot of the agriculturally active chemical, and (e) depositing the aliquot into the dried preform.

The aliquot of the agriculturally active chemical may be injected, sprayed, dropped or otherwise deposited into the container-like preform. The protective coating on the preform may be placed about the core or body portion as set forth above. A second dough including water and the second water dispersible agriculturally inert and essentially nontoxic composition is provided and applied in a layer about the dried body portion. The layer of the second dough about the body portion is then dried.

Pursuant to another feature of the present invention, a layer of a water soluble polymer is applied between the body portion and the protective coating. The polymer preferably comprises one or more of the following: acrylics, polyvinylidene chloride, ionomer, polyvinylalcohol, and polyethylhydroxycellulose and may be applied by spraying, rolling, dipping, or brushing.

An alternative method in accordance with the present invention for making a delivery system for an agriculturally active chemical comprising the steps of providing a first dough including water and a first water dispersible agriculturally inert and essentially nontoxic composition, extruding the dough to form a tube, and drying the tube. A second dough including water, a second water dispersible agriculturally inert and essentially nontoxic composition and a predetermined amount of the agriculturally active chemical is then formed as a core inside the dried tube. The core is dried and the tube with the core is then cut to form a plurality of segments. The ends of the segments are capped with dough including water and a third water dispersible agriculturally inert and essentially nontoxic composition. Subsequently, the capped ends of the segments are dried.

Yet another method for making a delivery system for an agriculturally active chemical comprising, in accordance with the present invention, the steps of providing a first dough including water and a first water dispersible agriculturally inert and essentially nontoxic composition, extruding the dough to form a tube, drying the tube and cutting the tube to form a plurality of tubular segments. A second dough including water, a second water dispersible agriculturally inert and essentially nontoxic composition and a predetermined amount of the agriculturally active chemical is provided and formed as a core inside each of the segments. The core inside each of the segments is then dried, the ends of the segments are capped with dough including water and a third water dispersible agriculturally inert and essentially nontoxic composition, and the capped ends are dried.

A delivery system in accordance with the present invention is substantially non-toxic. Agriculturally active chemicals can be applied to a garden or crop without human beings coming into significant contact with the chemicals.

Moreover, a delivery system in accordance with the present invention provides for a delayed release of the agriculturally active chemicals. The chemicals may be released by the gradual dispersion of water-dispersible carrier materials, namely, the agriculturally inert and essentially nontoxic compositions. In the dried state of the formed carrier bodies, the compositions in accordance with the present invention are tough and flexible and can be formed, e.g., molded, pressed, sculpted or otherwise manipulated, into a variety of different shapes.

It is to be noted that a delivery system in accordance with the present invention involves basically a biodegradable carrier and can be used to apply a biodegradable pesticide. The biocide pesticide, whether a herbicide, fungicide, insecticide or nemacide, can itself be biodegradable or genetically engineered. The biocide or pesticide disperses upon dispersion of the carrier and diffuses into the soil or water.

BRIEF DESCRIPTION OF THE DRAWING

FIG. 1 is a cross-sectional view of a pellet, in accordance with the present invention, for use in delivering an agriculturally active chemical.

FIG. 2 is a cross-sectional view of another pellet, in accordance with the present invention, for use in delivering an agriculturally active chemical.

FIG. 3 is a cross-sectional view of a cup-shaped device, in accordance with the present invention, for use in delivering an agriculturally active chemical.

DETAILED DESCRIPTION

Figure 4:
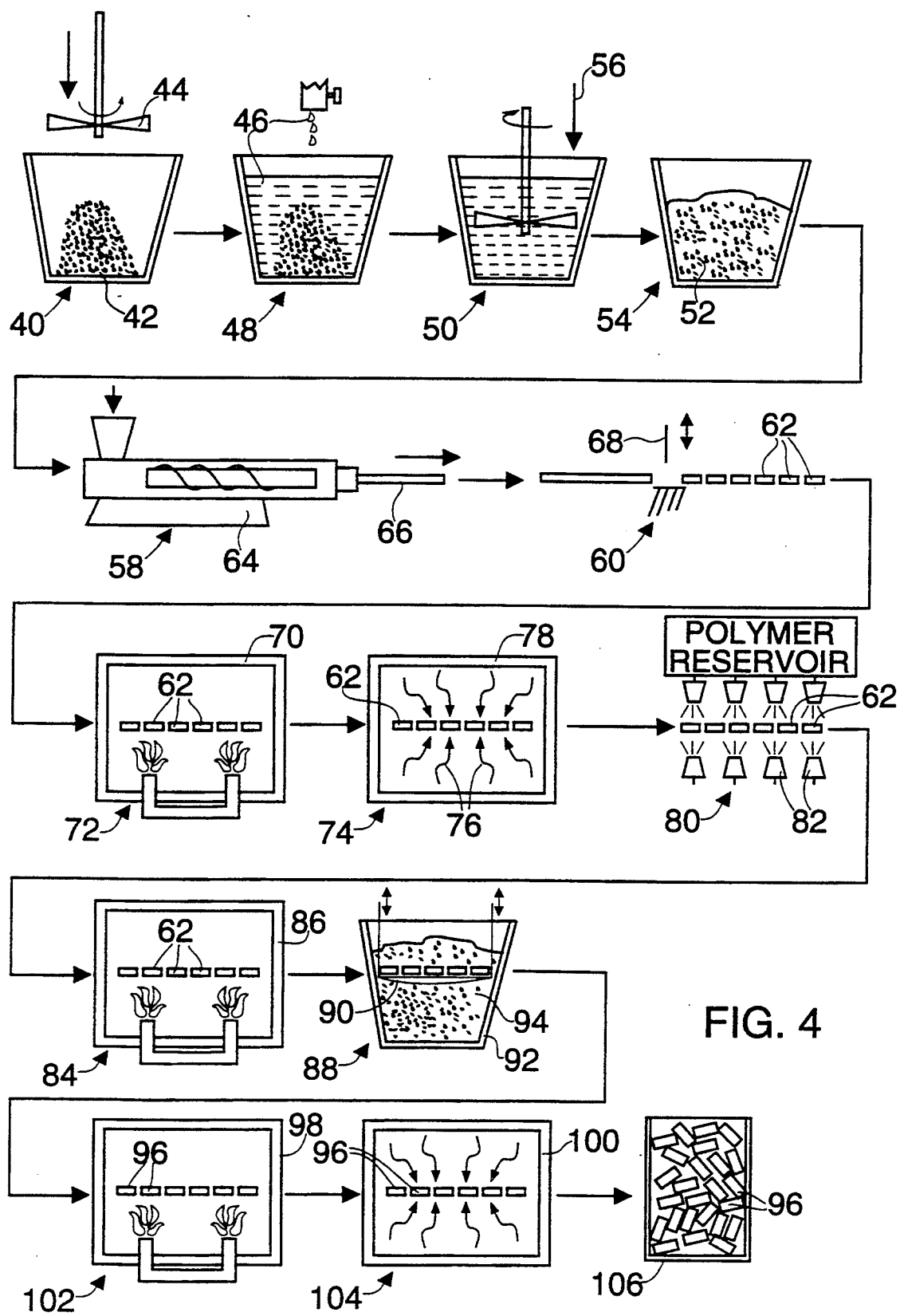
FIG. 4 is a diagram illustrating successive steps in the manufacture of the chemical bearing pellet of FIG. 1.

As illustrated in FIG. 1, a pellet 10 for use in agriculture or home gardening to deliver an agriculturally active chemical comprises a central body portion or core 12 made essentially of a water dispersible agriculturally inert and essentially nontoxic material which contains a predetermined aliquot of the agriculturally active chemical. The agriculturally active chemical is contained in core portion 12 in an amount effective to substantially terminate the functioning of a significant number of target agricultural pests upon dissolution of a selected number of pellets 10 in a predetermined volume of water and application of the resulting solution to soil.

Pellet 10 further comprises a protective outer coating 14 about the chemical-bearing core 12. The coating 14 is made of a second water dispersible agriculturally inert and essentially nontoxic composition which may either be the same as or different from the water-dispersible carrier composition of the core 12.

The agriculturally active chemical may be interspersed essentially homogeneously throughout core 12. Alternatively, the distribution of the agriculturally active chemical in the agriculturally inert and essentially nontoxic composition of core 12 may vary along a gradient from the center of core 32 to the periphery thereof. In that event, core 12 may take the form of a small cup or hollow receptacle, the agriculturally active chemical being deposited inside the cup or receptacle during manufacture.

Where the agriculturally active chemical is interspersed throughout the core, the chemical is more gradually released to the environment upon dispersion of the agriculturally inert and essentially nontoxic carrier composition of the core.

As further illustrated in FIG. 1, pellet 10 also comprises a layer 16 of polymeric material between core 12 and outer coating 14. Polymeric layer 16 serves to prevent or inhibit diffusion of the agriculturally active chemical from core 12 to coating 14.

Pellet 10 may take virtually any size or shape. Generally, for ease of production, a cylindrical shape is considered desirable. As described hereinafter with reference to FIG. 4, the cylindrical shape of core 12 is easily produced by extrusion. The size of pellet 10 and particularly of core 12 is largely arbitrary and depends in part on how much of the agriculturally active chemical is to be carried in each pellet. The amount of the agriculturally active chemical in turn depends on the particular chemical involved and on the particular end use application, for example, whether the pellet is intended for home use or agricultural use.

Coating 14 facilitates handling of the pellets 10 inasmuch as no special or extraordinary precautions need be taken. Coating 14 is nontoxic and serves as a temporary barrier to the diffusion of the agriculturally active chemical from core 12. This barrier function is also performed by polymeric layer 16.

In using pellets 10, a home owner, gardener, farm hand, etc., first determines the size of the area to be treated with the agriculturally active chemical. A number of pellets 10 is selected by the user in accordance with the size of the application. Thus, doubling the area to be protected generally requires double the number of pellets. The selected pellets are simply placed into a container of water and allowed to disperse. Upon dispersion of the pellets, the agriculturally active chemical becomes dissolved in the water. The residue from the agriculturally inert and essentially nontoxic compositions is partially dissolved, partially suspended in solution and may precipitate out to a minor extent. The residue, however, is essentially completely dispersible in water and does not clog spraying or other application equipment.

As depicted in FIG. 2, another pellet 20 for use in agriculture or home gardening to deliver an agriculturally active chemical comprises a central body portion or core 22 and a protective outer coating 24 without an intermediate polymeric layer as shown in FIG. 1. As described hereinabove, with reference to FIG. 1, core 22 comprises a water dispersible agriculturally inert and essentially nontoxic material which contains a predetermined aliquot of the agriculturally active chemical. The agriculturally active chemical is contained in core 22 in an amount effective to substantially terminate the functioning of a significant number of target agricultural pests upon dissolution of a selected number of pellets 20 in a predetermined volume of water and application of the resulting solution to soil, plants, a body of water, etc. Coating 24 is made of a second water dispersible agriculturally inert and essentially nontoxic composition which may either be the same as or different from the water-dispersible carrier composition of the core 22.

The pellet 20 of FIG. 2 may be useful in cases where the storage time of the pellets, i.e., the interval between manufacture and use, is not expected to be of especially long duration. In that case the pellets 20 can be handled safely without fear of contamination by the agriculturally active chemical. It is to be noted that the thickness of outer coating 24 may be varied in this case to provide a greater distance that the agriculturally active chemical must diffuse in order to reach the surface of the pellet 20.

As shown in FIG. 3, a delivery system or device takes the form of a cup or pot 30 comprising a cup-shaped central body portion or core 32, a protective outer coating 34, and an optional intermediate polymeric layer 36. In use, a seedling or young vegetable specimen is planted in pot 30, for example at a shipping center. The seedling with pot 30 is subsequently planted in soil at a destination or ultimate use station. As the pot 30 gradually dissolves or disperses in the soil in response to rain and waterings, the agriculturally active chemical gradually diffuses into the soil about the roots of the seedling and serves to kill, destroy or terminate nematodes or other agricultural pests.

Core 32 is made essentially of a water dispersible agriculturally inert and essentially nontoxic material which contains a predetermined aliquot of the agriculturally active chemical. The agriculturally active chemical may be interspersed substantially uniformly thoughout core 32 and is in an amount effective to substantially terminate the functioning of a significant number of target agricultural pests such as nematodes upon gradual dissolution of pot 30.

Pot 30 further comprises a protective outer coating 34 about the chemical-bearing core 32. The coating 34 is made of a second water dispersible agriculturally inert and essentially nontoxic composition which may either be the same as or different from the water-dispersible carrier composition of the core 32.

Pot 30 may take virtually any size or shape. Core 32 is preferably produced by press molding or injection molding a dough of the respective agriculturally inert and essentially nontoxic composition containing a predetermined concentration of the agriculturally active chemical. However, other techniques may be used, depending, for example, on the number of pots to be produced and the sizes and shapes of the pots. A small number of symmetrical chemical-delivery pots may be produced, for instance, by throwing on a potter's wheel.

Upon formation, core 32 is dried in a convection oven and additionally or alternatively in a microwave oven. If polymeric layer 36 is to be used, to provide delayed diffusion of the agriculturally active chemical from core 32 to coating 34, liquified polymer is then applied to the core by spraying, rolling, dipping, or brushing. The polymeric layer 36 is dried before the application of the outer coating 34. Preferably, coating 34 is molded onto the core 32. Alternatively, core 32 (with polymeric layer 36) may be dipped into a vat of the dough for forming the outer coating 34, provided that the dough is wet enough to adhere in a layer like coating to core 32 during a dipping process. Several dippings with alternate drying steps may be undertaken to ensure a coating 34 which is sufficiently thick.

The agriculturally active chemical is preferably a biocide such as an insecticide, fungicide or nemacide. More particularly, the agriculturally active chemical is a compound taken from the group consisting of propoxur, chlorpyrifos, diazinon, malthlon, carbaryl, fenvalerate, methomyl, acephate, permethrins, and diflubenzuron.

Following are several examples with parts indicated by weight of the water dispersible agriculturally inert and essentially nontoxic compositions for use in cores 12, 22, and 32 and coatings 14, 24, and 34.

EXAMPLE 1

35 parts cellulose ether
10 parts zinc stearate
10 parts cellulose tissue fiber

When combined with water to form a dough and then heated in a sheet-like form (1/16–1/8 inch) in a convection oven at approximately 200° C., this composition dries to form a web which is as hard and tough as shoe leather and yet can disperse in water within hours or days.

EXAMPLE 2

35 parts cellulose ether
10 parts zinc stearate
10 parts unbleached cellulose fiber When combined with water to form a dough and then heated in a sheet-like form (1/16–1/8 inch) in a convection oven at approximately 200° C., this composition also dries to form a hard and tough water-dispersible material.

EXAMPLE 3

19 parts cellulose ether
6 parts zinc stearate
100 parts water-saturated cellulose tissue fiber
10 parts calcium carbonate (e.g., SUPER FLEX 200)

In this composition, the cellulose tissue fiber is water saturated in order to facilitate shredding of the tissue into small (on the order of hundredths of a square inch) segments.

EXAMPLE 4

27 parts cellulose ether
8 parts zinc stearate
100 parts water-saturated cellulose tissue fiber
10 parts calcium carbonate (e.g., SUPER FLEX 200)
10 parts polyvinylalcohol (e.g., VINOL 203)

In this composition, the cellulose tissue fiber is water saturated also in order to facilitate shredding of the tissue into small segments. It is to be noted that the agriculturally inert and essentially nontoxic composition of this example, when heated as a 1/16 inch to 1/8 inch slab of dough in a convectional oven at 60° C. and then subjected to microwave radiation, forms a styrofoam-like material which is flexible and yet tough so that it is not as prone to cracking as styrofoam.

EXAMPLE 5

27 parts cellulose ether
8 parts zinc stearate
100 parts cellulose tissue fiber (water-saturated, then squeezed out by hand)

This composition, when mixed with water to form a dough and then heated as a 1/16 inch to 1/8 inch slab of dough in a convectional oven at 60° C. and then subjected to microwave radiation, forms a flexible and tough material.

EXAMPLE 6

27 parts cellulose ether
8 parts zinc stearate
100 parts cellulose tissue fiber (water-saturated, then squeezed out by hand)
20 parts polyvinylalcohol (e.g., VINOL 203)

This composition, when mixed with water to form a dough and then heated as a 1/16 inch to 1/8 inch slab of dough in a convectional oven at 60° C. and then subjected to microwave radiation, also forms a flexible and tough material.

As illustrated in FIG. 4 at 40, in manufacturing a chemical delivery pellet or device from the compositions any of the above-listed examples, one first mixes the dry ingredients in the respective amounts to make a substantially uniform mixture 42. Mixing may be accomplished automatically, as schematically illustrated at 44. Upon formation of the uniform mixture 42, water 46 and any wetted ingredients (not shown) are then added to the dry mixture in a step 48. In a subsequent step 50, the water 46 and the wet ingredients are mixed with the dry ingredients of mixture 42 to form a dough 52 (step 54) of the desired consistency. The consistency depends in part on the technique for forming the pellet and the size of the pellet. To the dough is added the liquid agriculturally active chemical, as indicated at step 48 by an arrow 56.

To determine an appropriate amount of the agriculturally active chemical, one selects first a unit dose of the chemical, that is, the smallest dose which may be used in any contemplated application. This dose corresponds to one pellet. If, for example, one teaspoon of a particular agriculturally active chemical (e.g., from the above-listed chemicals) is added to ten gallons of water in accordance with the manufacturer's directions, but a smallest dose might be two gallons for a limited application (e.g., home use), then one teaspoon of the agriculturally active chemical is to be added to an amount of the core dough which will make five pellets. If the pellet size is selected to be about 28 grams, then the agriculturally active chemical is added to the dough in an amount so that one teaspoon of the chemical corresponds to 140 grams of the initial mixture.

The dose sizes for the different agriculturally active chemicals, e.g., propoxur, chlorpyrifos, diazinon, malthlon, carbaryl, fenvalerate, methomyl, acephate, permethrins, and diflubenzuron, are available from the respective manufacturers.

Upon the formation of dough 52 containing the appropriate amount of the respective agriculturally active chemical, the dough is manipulated in steps 58 and 60 to form pellets 62 of the predetermined size and shape. More particularly, an extruder 64 is operated to extrude a rod 66 of a predetermined thickness. In step 60, rod 66 is cut by a reciprocating blade 68.

Pellets 62 are conveyed to a convection oven 70 for drying in a step 72. The drying temperature in convection oven 70 is in a range between approximately 50° C. and approximately 300° C. The lower end of the temperature range is selected in the event that the pellets 62 are subjected in a subsequent step 74 to microwave radiation 76 in a microwave oven 78.

It is to be noted that cutting step 60 and drying steps 72 and 74 may be reversed, in which case reciprocating cutting blade 68 is replaced by a saw blade (not shown).

After drying of pellets 62 in steps 72 and 74, a polymeric layer is applied in a step 80 via spray nozzles 82. Alternatively, the polymeric layer is applied via a rolling, brushing, or dipping operation. In a subsequent step 84, the polymeric layer is dried in an oven 86.

As discussed above with reference to FIG. 2, the polymeric layer may be omitted. In that case, pellets 62 are conveyed from ovens 70 and 78 directly to a dipping step or station 88.

In dipping step 88, dried pellets 62 are lowered via an elevator device 90 into a vat 92 containing a dough 94 made from a water dispersible agriculturally inert and essentially nontoxic composition such as one of the compositions listed in the examples above. Dough 94 is substantially more fluid than dough 52, whereby the dough coats about pellets 62 to form new pellets 96.

Coated pellets 96 are dried in a convection oven 98 and, optionally, a microwave oven 100 in a pair of consecutive steps 102 and 104. Steps 88, 102 and 104 may be performed several times to provide pellets 96 with coatings of a predetermined desired thickness. As discussed hereinabove, the thickness of the protective coatings on the pellets 96 may be increased (particularly in the case of the pellet 20 shown in FIG. 2) to augment the barrier function of the coating.

Protective coatings 14 and 24 may be provided on cores 12 and 22 in ways other than that shown in steps 88, 102 and 104 of FIG. 4. For example, coatings 14 and 24 may be formed by rolling the cores in the coating dough or, particularly in the case of large pellets, molding the coating dough about the cores.

A load of pellets 96 may be shipped in a container 106. No special or extraordinary precautions need be taken for the disposition of container 106 after use of pellets 96 contained therein. The pellets 10, 20, 96 themselves may be handled by hand without danger of contamination by the agriculturally active chemical.

From the above examples, it is seen that the various components of the agriculturally inert and essentially nontoxic compositions have weight percentage ranges as follows. The cellulose fiber, whether in the form of shredded tissue paper or unbleached cellulose fiber, preferably comprises between approximately 20% and 75% by weight of the respective water dispersible agriculturally inert and essentially nontoxic composition, whether used in the core 12 (FIG. 1), 22 (FIG. 2) or 32 (FIG. 3) of the chemical delivery pellet or article or in the protective outer coating 14, 24 or 34. The cellulose ether preferably comprises between approximately 10% and 65% by weight of the composition. In addition, the zinc stearate preferably comprises between approximately 4% and 25% by weight of the composition. Calcium carbonate preferably comprises between approximately 0% and 10% of the respective water dispersible agriculturally inert and essentially nontoxic composition, while polyvinylalcohol preferably comprises between approximately 0% and 15% of the respective water dispersible agriculturally inert and essentially nontoxic composition.

In the manufacturing method illustrated in FIG. 4, if rod 66 takes the form of a tube, a core may be formed inside the tube upon the drying thereof, the core being a water-dispersible agriculturally inert and essentially nontoxic composition of one of the above examples containing a predetermined amount of the selected agriculturally active chemical. The core may be formed by injecting or otherwise depositing a dough made of the selected agriculturally inert and essentially nontoxic composition and containing the selected agriculturally active chemical. The core is dried and the tube with the core is cut to form a plurality of segments. Alternatively, the tube may be cut prior to the deposition or insertion of the chemical-bearing dough. The ends of the segments are capped with another dough including water and a water dispersible agriculturally inert and essentially nontoxic composition. Subsequently, the capped ends of the segments are dried.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A delivery system for a biocide comprising:
   a body portion including a first water dispersible agriculturally inert and essentially nontoxic composition containing an amount of the biocide effective to substantially terminate the functioning of a significant number target agricultural pests upon application of said biocide to a substrate via the delivery system, said body portion having a predetermined size and a predetermined shape; and
   a protective coating, about said body portion, of a second water dispersible agriculturally inert and essentially nontoxic composition,
   wherein at least one of said first or second water dispersible compositions includes a cellulose ether, stearic acid or one of its related salt compositions and cellulose fiber.

2. The delivery system defined in claim 1 wherein said body portion takes the shape of a pellet.

3. The delivery system defined in claim 1 wherein said body portion takes the form of a container.

4. The delivery system defined in claim 3 wherein said container is cup-shaped.

5. The delivery system defined in claim 1 wherein said biocide is interspersed throughout said first water dispersible agriculturally inert and essentially nontoxic composition.

6. The delivery system defined in claim 1 wherein said body portion is hollow and defines a chamber, said biocide being disposed at least partially within said chamber.

7. The delivery system defined in claim 1 wherein said compound biocide is a taken from the group consisting of dimethoate, vydate, vendex, metasystox-R, fluvalinate and kethane, invermectin, propoxur, chlorpyrifos, diazinon, malathion, carbaryl, fenvalerate, methomyl, acephate, permethrins, and diflubenzuron.

8. The delivery system defined in claim 1 wherein said first or second water dispersible agriculturally inert and essentially nontoxic compositions includes:
   zinc stearate as said salt composition of stearic acid.

9. The delivery system defined in claim 8 wherein said cellulose fiber is between approximately 20% and 75% by weight of said one of said first water dispersible agriculturally inert and essentially nontoxic composition and said second water dispersible agriculturally inert and essentially nontoxic composition.

10. The delivery system defined in claim 8 wherein said cellulose ether is between approximately 10% and 65% by weight of said one of said first water dispersible agriculturally inert and essentially nontoxic composition and said second water dispersible agriculturally inert and essentially nontoxic composition.

11. The delivery system defined in claim 8 wherein said zinc stearate is between approximately 4% and 25% by weight of said one of said first water dispersible agriculturally inert and essentially nontoxic composition and said second water dispersible agriculturally inert and essentially nontoxic composition.

12. The delivery system defined in claim 8 wherein said cellulose fiber is shredded tissue paper.

13. The delivery system defined in claim 8 wherein said cellulose fiber is unbleached cellulose fiber.

14. The delivery system defined in claim 8 wherein said one of said first water dispersible agriculturally inert and essentially nontoxic composition and said second water dispersible agriculturally inert and essentially nontoxic composition further includes calcium carbonate.

15. The delivery system defined in claim 14 wherein said calcium carbonate is between approximately 0% and 10% of said one of said first water dispersible agriculturally inert and essentially nontoxic composition and said second water dispersible agriculturally inert and essentially nontoxic composition.

16. The delivery system defined in claim 8 wherein said one of said first water dispersible agriculturally inert and essentially nontoxic composition and said second water dispersible agriculturally inert and essentially nontoxic composition further includes polyvinylalcohol.

17. The delivery system defined in claim 16 wherein said polyvinylalcohol is between approximately 0% and 15% of said one of said first water dispersible agriculturally inert and essentially nontoxic composition and said second water dispersible agriculturally inert and essentially nontoxic composition.

18. The delivery system defined in claim 8 wherein said second water dispersible agriculturally inert and essentially nontoxic composition is different from said first water-dispersible agriculturally inert and essentially nontoxic composition.

19. The delivery system defined in claim 8 wherein said second water dispersible agriculturally inert and essentially nontoxic composition is substantially the same as said first water-dispersible agriculturally inert and essentially nontoxic composition.

20. The delivery system defined in claim 8 wherein said first water dispersible agriculturally inert and essentially nontoxic composition further includes a surfactant.

21. The delivery system defined in claim 8, further comprising a layer of a water soluble polymer between said body portion and said coating.

22. The delivery system defined in claim 21 wherein said polymer is taken from the group comprising acrylics, polyvinylidene chloride, ionomer, polyvinylalcohol, and polyethylhydroxycellulose.

* * * * *